(12) United States Patent
Luce

(10) Patent No.: US 9,084,696 B2
(45) Date of Patent: Jul. 21, 2015

(54) ABSORBENT ARTICLE FOR AN OSTOMY GUARD

(71) Applicant: Donna E. Luce, Duncanville, TX (US)

(72) Inventor: Donna E. Luce, Duncanville, TX (US)

( * ) Notice: Subject to any disclaimer, the term of this patent is extended or adjusted under 35 U.S.C. 154(b) by 211 days.

(21) Appl. No.: 13/841,269

(22) Filed: Mar. 15, 2013

(65) Prior Publication Data

US 2014/0276519 A1    Sep. 18, 2014

(51) Int. Cl.
| | | |
|---|---|---|
| *A61F 13/15* | (2006.01) | |
| *A61F 5/44* | (2006.01) | |
| *A61F 13/02* | (2006.01) | |
| *A61F 13/00* | (2006.01) | |

(52) U.S. Cl.
CPC . *A61F 13/02* (2013.01); *A61F 5/44* (2013.01); *A61F 2013/00412* (2013.01)

(58) Field of Classification Search
CPC .. A61F 5/44; A61F 5/4401; A61F 2005/4402
USPC .................................. 604/361, 33, 333, 334
See application file for complete search history.

(56) References Cited

U.S. PATENT DOCUMENTS

| | | |
|---|---|---|
| 1,922,763 A | 8/1933 | Gricks |
| 2,129,054 A | 9/1938 | Geisler |
| 2,496,175 A | 1/1950 | Perry |
| 2,549,649 A | 4/1951 | Van Hove |
| 2,656,838 A | 10/1953 | McConnell |
| 2,675,002 A | 4/1954 | Cesare |
| 2,837,094 A | 6/1958 | Cowles |
| 3,074,404 A | 1/1963 | Robinson |
| 3,398,744 A | 8/1968 | Hooper |
| 4,596,566 A | 6/1986 | Kay |
| 4,636,206 A | 1/1987 | Ederati |
| 4,723,952 A | 2/1988 | Esposito |
| 4,738,257 A | 4/1988 | Meyer |
| 4,867,749 A | 9/1989 | Steer |
| 5,125,917 A | 6/1992 | Whealin |
| 5,178,614 A | 1/1993 | McDowell |
| 5,203,806 A * | 4/1993 | Broida .......................... 604/338 |
| 5,338,315 A | 8/1994 | Baker |
| 5,653,701 A | 8/1997 | Millman |
| 5,811,116 A | 9/1998 | Gilman |
| 6,129,715 A | 10/2000 | Cunningham |
| 8,316,985 B2 | 11/2012 | Bain et al. |
| 2007/0135783 A1 | 6/2007 | Scott |
| 2010/0191202 A1 | 7/2010 | Hogard et al. |
| 2010/0241093 A1 | 9/2010 | Hooper |

FOREIGN PATENT DOCUMENTS

WO        9716141        5/1997

* cited by examiner

*Primary Examiner* — Jacqueline Stephens

(74) *Attorney, Agent, or Firm* — Hemingway & Hansen, LLP; D. Scott Hemingway

(57) ABSTRACT

A disposable absorbent article for use with ostomy appliances and complementary to a guard system such as has been illustrated, that provides an additional level of security and comfort to an ostomate already utilizing a two-piece or one-piece ostomy appliance of the type which is secured to the body with a faceplate comprising an adhesive securement means such as a hydrocolloid adhesive member or a combination of hydrocolloid adhesive member and an integral or non-integral adhesive non-woven fabric or adhesive tape.

19 Claims, 10 Drawing Sheets

ABSORBENT ARTICLE FOR AN OSTOMY GUARD

CROSS REFERENCE TO RELATED APPLICATIONS

Not applicable.

STATEMENT REGARDING FEDERALLY SPONSORED RESEARCH OR DEVELOPMENT

Not applicable

TECHNICAL FIELD

This invention relates to disposable absorbent devices for use with ostomy appliances.

BACKGROUND OF THE INVENTION

A discussion of ostomies, ostomy appliances and their problems are critical to understanding what is required and desirable in an absorbent article for incontinent ostomates and their ostomy appliances, that as a result of many uncontrollable factors are limited in their ability to retain natural discharges such as urine or excretement, due to leakage of primary means.

Disposable absorbent devices such as adult incontinence pads, sanitary pads, or pantiliners are provided for the population whose bodily wastes are eliminated thru natural pathways rather than artificial means such as ileostomies, colostomies, or urostomies. An ostomy provides fecal or urinary diversion in emergent and elective settings and is a surgically created opening in which a portion of the intestine is brought through the abdominal wall to form a stoma that may be permanent or temporary depending on the reason for surgery, i.e., disease, injury, birth defects, or cancer.

Pouching systems (also called appliances) are used to collect bodily waste through the surgically created openings on the abdomen. Optimal stoma placement on the abdomen takes into consideration a position within the abdominus rectus muscle (the six pack muscle), usually to the right or left of the belly button, below a beltline, avoiding skin folds, scars, and bony prominences among other considerations. Incorrect stoma placement, or emergent procedures without benefit of proper planning, may create difficulties in attaching or maintaining adhesion of a pouching system (appliance), causing leakage of waste, peristomal skin inflammation, and many other hardships including stress and increased costs.

Although appliance styles vary from manufacturer to manufacturer, there are two main types of pouching systems commercially available: one piece systems consisting of a pouch with a built-in skin barrier (also called a faceplate), and two-piece appliances composed of a faceplate and detachable pouch. A flange is provided on the two-piece system in the form of a pair of annular or ring-like rigid plastic parts designed to aid in either securing the pouch to the faceplate or removing the pouch at the user's discretion.

A one-piece system connects the faceplate to the pouch by welding or heat sealing. Faceplates have an adhesive layer formed of a soft, skin-friendly hydrocolloid containing adhesive material and provide therein a centrally located aperture to receive a stoma. Systems may further provide a peel and stick tape on the outer edges of a faceplate for additional adhesion. Sticky skin wipes also help with adhesion of the appliance faceplate and said faceplates are attached to the peristomal region of the user to protect the skin from irritating digestive juices. A pouch may or may not be equipped with a drainable end.

Ostomates are faced with many problems associated with stomas and stoma waste collection pouches. One critical problem faced by ostomates is loss of adhesion of the faceplate from the skin, threatening a resulting loss of containment of waste. A faceplate cannot be checked for properly secured adhesion once it is applied to the skin. An itchy, irritated feeling may be the only warning, if any, that a problem has developed behind a faceplate.

Loss of adhesion is common and unpredictable, even when directions for use are strictly followed. Subsequent leakage of waste can and does occur, often without warning, soiling clothes, causing unpleasant odors, and embarrassment to the wearer. The wearer must immediately cease all activity and promptly address the situation, as flow of output is continuous and involuntary.

Uncontrollable factors such as perspiration, changes in weight, skin oils, watery discharge from food, and other influences such as sports, work, or even bending over to tie shoes may contribute to a loss of adhesion of a faceplate. Although considerations for stoma placement may be optimum, some part of an appliance faceplate may lie directly underneath the waistband of a wearer's clothing contributing to loss of adhesion. Fear of public humiliation due to such failures with the pouching adhesion causes many ostomates to avoid returning to normal lifestyle activities, including work and usual attire.

Another concern is the function of the peristalsis action of the digestive tract, as characteristically strong, wave like motions carry food through the intestines and out of the body. Especially in the presence of short, flush, or retracted stomas, this movement may contribute to acidic waste depositing behind a faceplate, affecting efficient emptying of output into a pouch, causing loss of adhesion.

An ongoing problem associated with ostomies are peristomal hernias that create an uneven platform for a faceplate to attach, creating yet another cause for faceplate failure.

Another problem is that form-fitted clothing pressed against the thin layers of a pouching system can restrict flow, and force output to regress behind a faceplate.

Another fear that ostomates or any incontinent person might dread, is the necessity of wearing a diaper to avoid the disdainful consequences of a leak in public or on bed linens while sleeping.

There remains a need to provide an absorbent article for the purpose of capturing escaping effluent in the event of a leaking ostomy appliance that for stated reasons, are limited in their ability to contain natural discharges or to provide complete, leak-free security at all times. The absorbent article must be able to absorb and contain viscous and liquid fluids.

SUMMARY OF THE INVENTION

A disposable absorbent article for use with ostomy appliances and complementary to a guard system such as has been illustrated, that provides an additional level of security and comfort to an ostomate already utilizing a two-piece or one-piece ostomy appliance of the type which is secured to the body with a faceplate comprising an adhesive securement means such as a hydrocolloid adhesive member or a combination of hydrocolloid adhesive member and an integral or non-integral adhesive non-woven fabric or adhesive tape.

DETAILED DESCRIPTION

Figure 1:
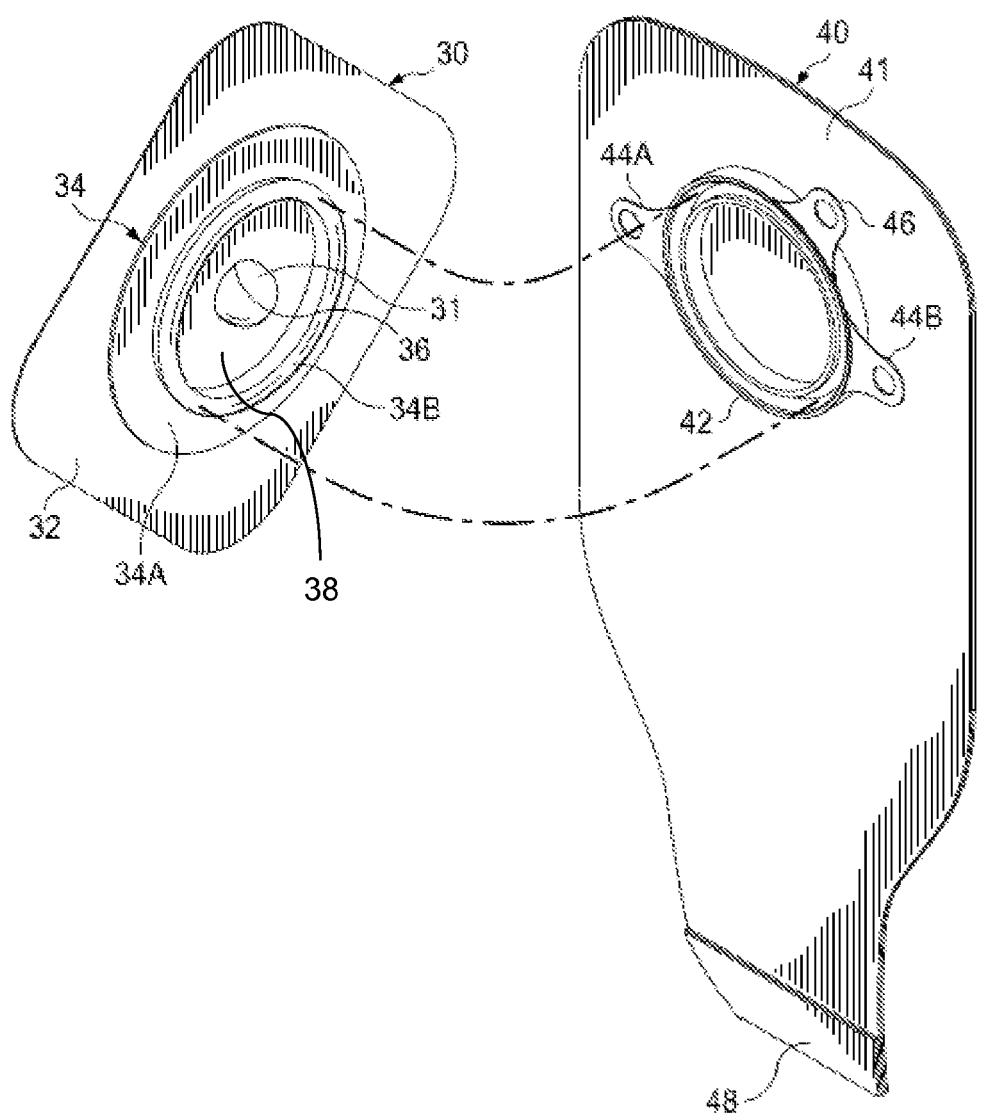
FIG. 1 is a perspective view of an ostomy appliance (pouching) system.

The illustration of FIG. 1 is given to allow for visual understanding of an ostomy appliance system and is not part of the invention of the present application.

FIG. 1 is a typical example of a current, commercially available two-piece ostomy pouching system consisting of a pouch 40, a pouch flange 42, belt tabs 44A and 44B (44B not shown) on either side of the pouch flange; a tab on the upper flange facilitates easy removal, and a fold and lock drain 48 for removal of waste. The two-piece appliance also consists of a faceplate 30, with coupling flange 34B and centrally located aperture 36 to receive a stoma 31. An outer taped portion 32 aids adhesion of an appliance faceplate on the abdomen.

Figure 2:
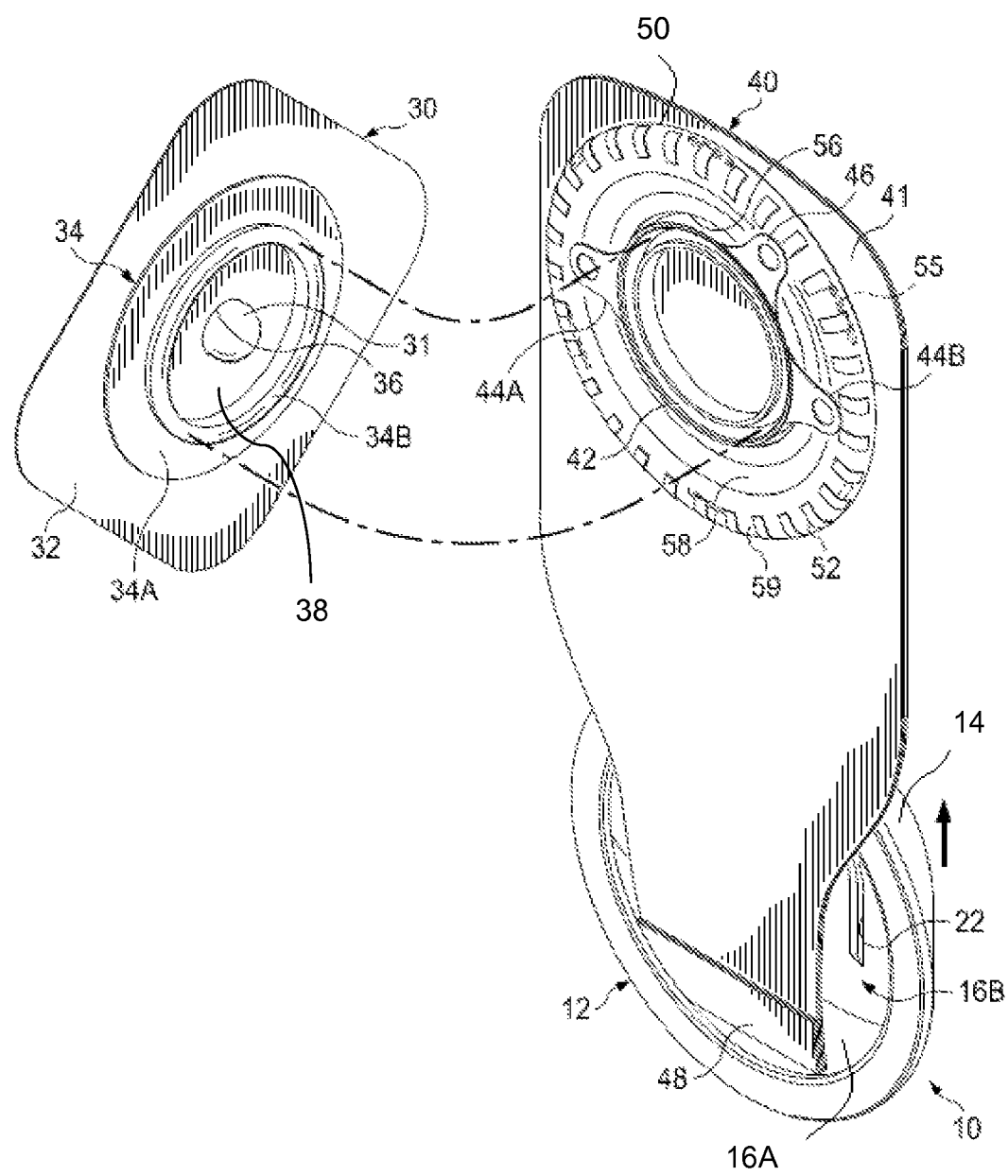
FIG. 2 is a perspective view of an ostomy appliance system of FIG. 1 and a guard system allowing current ostomy appliances to function as intended.
Figure 3:
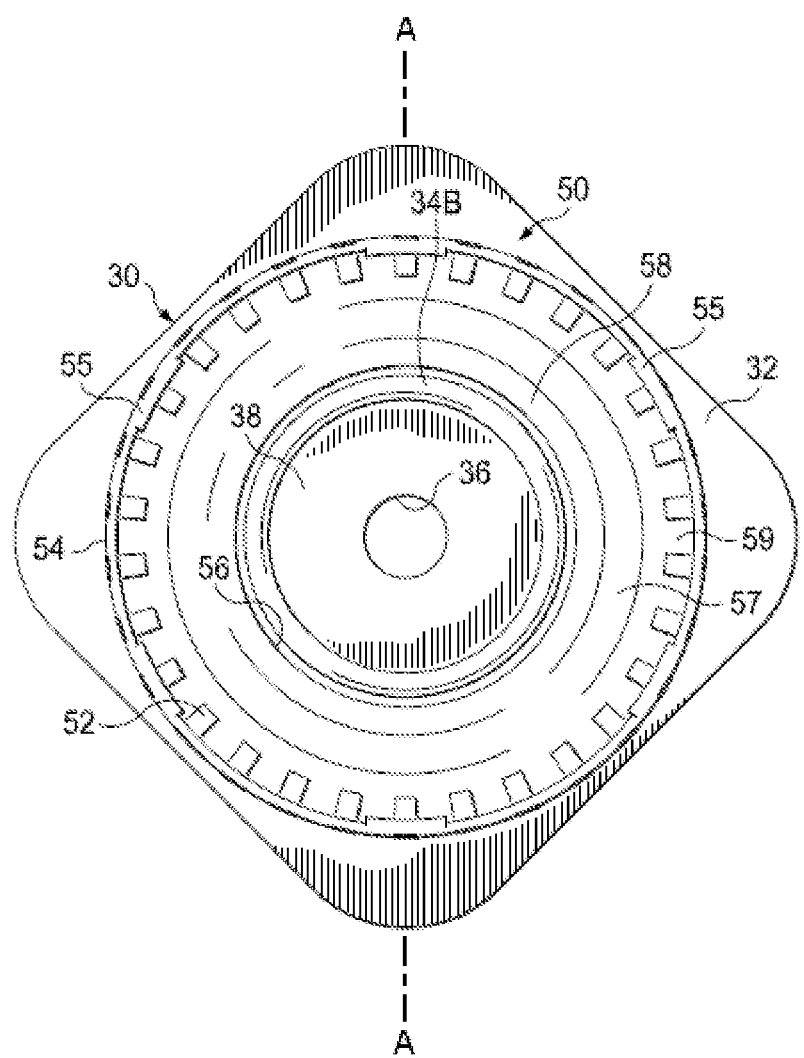
FIG. 3 is a front perspective view of an adapter of a guard system of FIG. 2 on the faceplate of an ostomy appliance.
Figure 4:
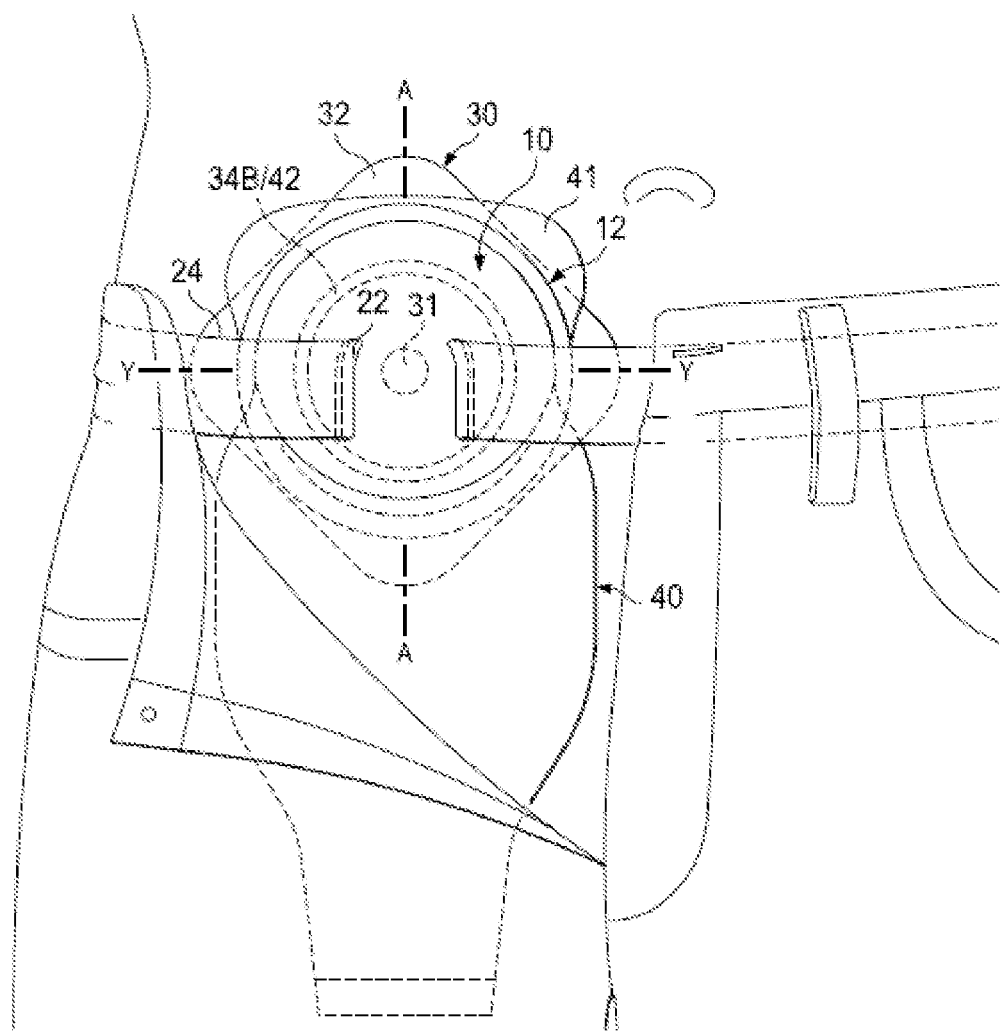
FIG. 4 is an environmental view of an ostomy appliance and guard system of FIG. 2 showing its intended position on the torso of a human.

One embodiment of the guard system 10/50 is shown in FIGS. 2-4, and a condensed description is given below, and an in depth description given in an international application PCT/US2012/046221. The first embodiment of an absorbent article is specifically for use with the guard system 10/50, and necessary details are given here to inform how, where, and why it is used with an ostomy appliance, the guard system's approximate size and physical structure in relation to the faceplate of an appliance, and is not part of the invention of the present application.

The exemplary guard system of FIG. 2 provides a secure boundary against loss of containment of bodily waste, helps a stoma to protrude, allows flow of output, aids adhesion of an appliance faceplate, and allows one to wear form-fitted clothing among other beneficial functions.

The ostomy appliance guard system illustrated in FIG. 2 is comprised of a guard 10 and an adapter 50. The adapter 50 is provided in various sizes in the centrally located aperture 56 to accommodate the various flange sizes of ostomy appliances currently available, and allows the guard 10 to remain a universal size. Appliance flanges are provided in common sizes between appliance manufacturers, but are not necessarily interchangeable. The adapter 50, shown already in place, illustrates that flange 42 of pouch 40 is snapped into place with complementary flange 34B of a faceplate 30.

The adapter 50 applied first, having the pouch end 48 guided through the rear of centrally located aperture 56, is lifted up and over the upper portion of a pouch 41, and aperture 56 is then circumferentially surrounding the now coupled appliance flanges 42 and 34B. Adapter 50, pressing inwardly on flange base 34, helps a stoma to protrude while preventing the flanges 42/34B from protruding into the body of the guard 10. Pouch tabs 44A, 44B and 46 may be removed for more efficient use of the guard system 10/50.

The guard 10 is applied in the same manner as adapter 50, and pouch end 48 is guided through rear central aperture 16B of guard 10, then out through front aperture 16A, the arrow indicates that guard 10 is then lifted upwards until body 14 of guard 10 encompasses the now engaged flanges including the upper pouch portion 41 (tucked inside guard body in use to prevent intestinal gasses from ballooning above a waistline of pants), and annular ring 12 of guard 10 and adapter 50 snap-fit together, into the adapter's guard receiving channel 59, in a mechanical interlock via adapter retaining ribs 55 enabling the guard system 10/50 to maintain it's position proximate a stoma 31.

The body 14 of the guard 10 allows unhindered flow of output. In case liquid output behind the faceplate 30 causes the hydrocolloid adhesive member 38 to loosen from the skin, the hydrocolloid adhesive member 38 may push into a cavity formed by sloping section 57 and support wall 58 and sealed by guard receiving channel 59 that provides a temporary reservoir for effluent, allowing the user time to change the appliance before escape of output occurs. A guard system 10/50 contacts a faceplate 30 more or less than about ¼ in (0.06 cm) inside the outer periphery of said faceplate. Adapter protrusions 52, on the body-facing side of an adapter 50, create discontinuous contact on a faceplate 30 facilitating blood flow in the non-contact areas and beneficially reducing an itchiness associated with continuous pressure on the skin.

Referring to FIG. 3, the adapter 50 is shown unaccompanied by the exemplary guard 10 of FIG. 2, and is shown with only an adapter 50, pointing out the close proximity of a guard system's outer circumference proximate the edge of outer taped portion 32 of a faceplate 30. A guard system aids adhesion of a faceplate preventing a sudden loss of containment, however, liquicious output is insidious and more difficult to contain than solid matter and small amounts of liquid may seep out from under the outer taped portion 32 of a faceplate 30, soiling a wearer's clothing or bed linens. Leakage always comes from under a faceplate unless there is a defect in the appliance itself, for instance, a hole in a heat seal of a one-piece appliance, or the plastic connection of a floating flange (which allows one to snap on a pouch without pressure on the abdomen), or leakage may come from accidental uncoupling or incomplete coupling of a pouch 40.

The first embodiment will illustrate an absorbent article having a greater thickness in the absorbent core that extends beyond the periphery of a user's preferred faceplate for the purpose of absorbing and blocking any liquid seepage emerging from under outer tape portion 32 of a faceplate 30 preventing embarrassing loss of containment. A continuous density throughout the absorbent core, and especially underneath the guard system 10/50, would detract from a significant and intended function of said guard system, because by design, the adapter 50 has a sloping section 57 that provides a temporary reservoir for effluent in the case liquid output behind a faceplate causes the hydrocolloid member 38 to loosen from the skin. An absorbent article with optimal fluid absorbency and excellent barrier properties against wetness next to the skin would bring peace of mind to a user as well as a preventative against soiling the user's clothing or bed linens. FIG. 4 shows the arrangement of a guard system, appliance, and faceplate on a torso (parts of the appliance and guard systems shown in phantom), illustrating a similar embodiment of the guard 10 that includes slits 22 and a security strap 24. A user may attach a faceplate 30 to the abdomen as shown in FIG. 4 with corners applied diagonally, as in a diamond shape, or may adjust it a quarter of a turn so that the faceplate 30 is in the shape of a square on the abdomen, and is done so, according to the unique situation of a user, applied in one way or the other in an attempt to derive greater security in areas prone to leak or that may even be herniated. Leaks usually emerge between corners of square, or generally square faceplates.

Figure 5:
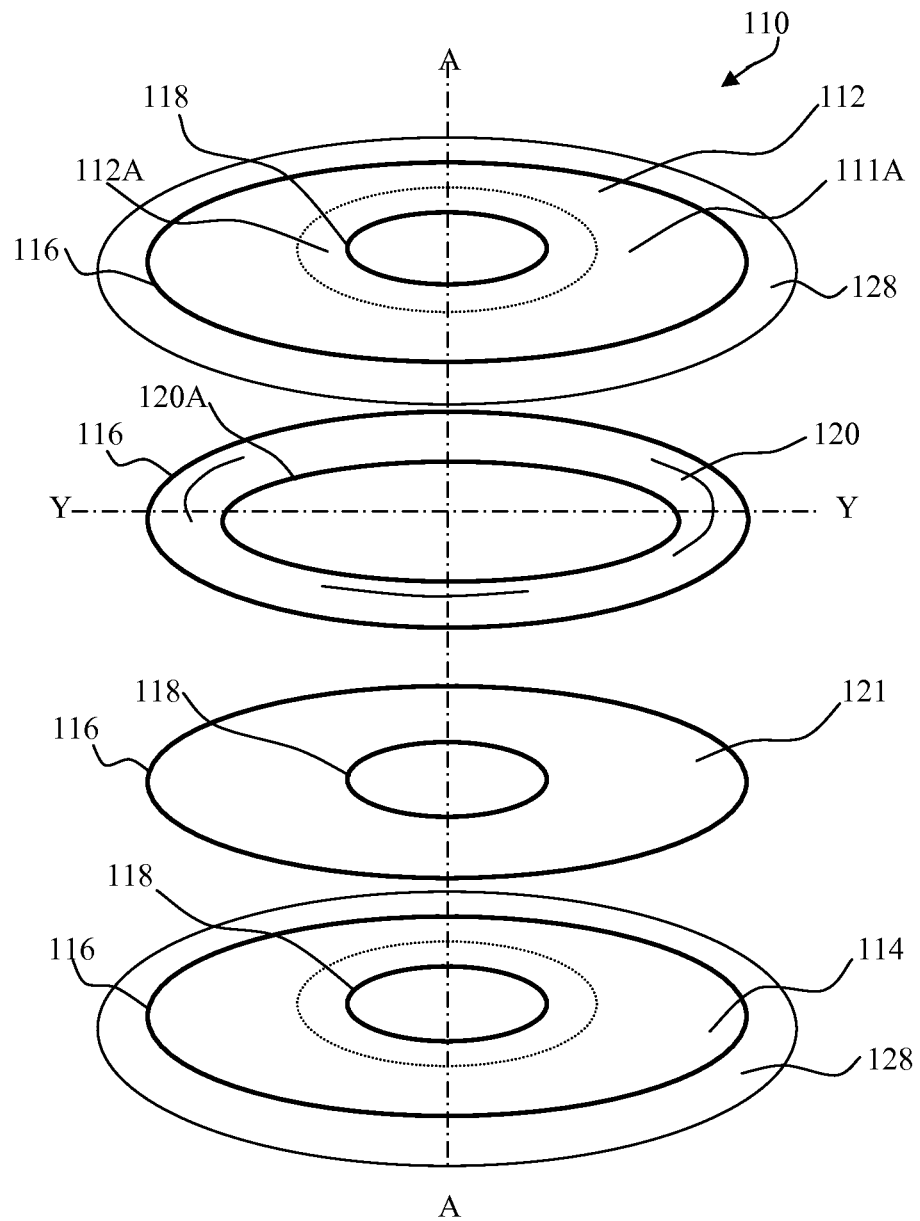
FIG. 5 is a front perspective view of the first embodiment of an absorbent article.

FIG. 5 illustrates the individual components of the absorbent article 110 and consists of two sides or two surfaces, a body facing side or body facing surface 111A, and a garment facing side or garment facing surface 111B (not shown), a fluid permeable top sheet 112, a fluid impermeable backsheet 114, and cores 120 and 121 interposed between. Absorbent core 121 may be a distribution or transfer sheet, its purpose well known in the art, and may be interposed between the topsheet 112 and outer core 120 or alternately, may be a web backing layer interposed between outer core 120 and backsheet 114, but all in accordance with the best mode of manufacture to accomplish the desired functions. Alternately, cores 120 and 121 may be one sheet with varied degree of thickness.

The absorbent article 110 also provides a centrally located aperture 118 through each member component of said absorbent article, for the purpose of maintaining a position upon a faceplate 30 of an ostomy appliance. Not having a flat configuration, outer core 120, has a greater radially extended absorbent core aperture 120A, in comparison to the other member components. The fluid permeable top sheet 112 and fluid impermeable backsheet 114 extend beyond the cores 120, 121 in at least a lateral direction and are joined to one another in the area outside said cores 120, 121 to form an edge seam 116 (and) and an outer border 128, and may be joined by gluing, crimping or heat-sealing completely around the periphery of the absorbent article, including sealing the edges of central aperture 118, secured by any means known in the art.

The outer border 128, having a front, or body facing border 128A, and a back, or garment facing border 128B, (not shown) may be supplied in any shape or form that provides the best protection against leakage if outer border 128 is utilized for taping the absorbent article 110 to the body.

The conjoined absorbent article 110 is applied in the same fashion as the guard system 10/50 by guiding the pouch end 48 of an ostomy pouch 40 through central aperture 118 of body facing surface 111A of the topsheet 112, and out garment facing surface 111B, and lifting the article up and over the upper portion of a pouch 41; central aperture 118 is then circumferentially surrounding the coupled appliance flanges 42/34B. The body facing surface 111A is intended to be worn adjacent the faceplate 30 of the wearer's preferred appliance. In the case of a one-piece appliance, central aperture 118 is placed generally adjacent the connection of the pouch to the faceplate (usually the heat weld) and body facing surface 111A lying on the faceplate 30.

FIG. 5 also shows the absorbent article 110 has two centerlines, a transverse (or lateral) centerline A-A and a longitudinal centerline Y-Y. The term "transverse" as used herein, refers to a line, axis, or direction in the plane of the absorbent article 110 that is generally aligned with (e.g., approximately parallel to) the abdomen of a wearer. The terms "longitudinal" used herein, refers to a line, axis or direction within the plane of the absorbent article 110 that is generally perpendicular to the transverse direction. In use, the absorbent article 110 is interposed between a faceplate and a pouch 40 and guard system 10/50 and is worn in a transverse direction along line A-A, i.e., generally parallel a user's abdomen.

The fluid permeable topsheet 112 may be made of a wide range of materials that are soft, non-irritating, woven or non-woven; an aperture formed layer which is permeable but having non-absorbent qualities to avoid moistness next to the skin, and may be used singularly or in conjunction with other woven or non-woven topsheet materials to further reduce the tendency for liquids to pass back through and rewet the wearer's skin. The topsheet 112 may be formed of any material known in the art to aid conveyance of liquid quickly to an absorbent core 120, with the capability to absorb a sudden increase of fluids.

Topsheet 112 of the absorbent article 110 may or may not comprise an adhesive means in the central portion 112A of the body facing surface 111A, for the purpose of attaching the absorbent article 110 to the faceplate 30 of a user's appliance. Strings of adhesive or a pattern of adhesive spots may adhere to various faceplate surfaces of polypropylene, polyethylene, polyvinyl chloride laminates, etc., or may attach by any other means, for example, hook and loop fastening means may attach to a woven or non-woven surfaces of appliance faceplates 30 or alternately, to the body facing side of a pouch 40.

The outer core 120 may consist of cellulosic fluff and super-absorbent polymers and other necessary components conveying a means to absorb bodily fluids and disposed over the backsheet 114 or absorbent core 121 as the case may be. The absorbent core 121 may be a non-woven backing layer and may be extended radially outwardly to the edge seam 116, from central aperture 118 as shown, or may extend only to the core aperture 120A of outer core 120, depending on manufacturing considerations and composition. Other absorbent core members may be added, whether layered above or below the outer core 120, hydrophobic or hydrophilic in nature, and may easily be selected by those skilled in the art and utilized in the best manner to carry out the manufacture of the absorbent article to provide the intended functions, including any suitable materials or processes in its construction, for instance, the absorbent article 110 may include anti-leak compression lines or transverse wicking that extend into the thickness of the article in this or other embodiments that may be worn without a guard system 10/50, provided that the absorbent article 110 has the overall characteristics described herein.

All layers may be thermally, mechanically or chemically bonded by any suitable method of bonding non-woven fabric that may be known in the art, such as, hot or belt calendering involving area, point or embossed bonding or ultrasonic means; thru-air or other known methods, choosing any variable components or bi-components of binding fibers, powders or webs in the construction and bonding processes, and as may be deemed necessary by those skilled in the art.

Figure 6:
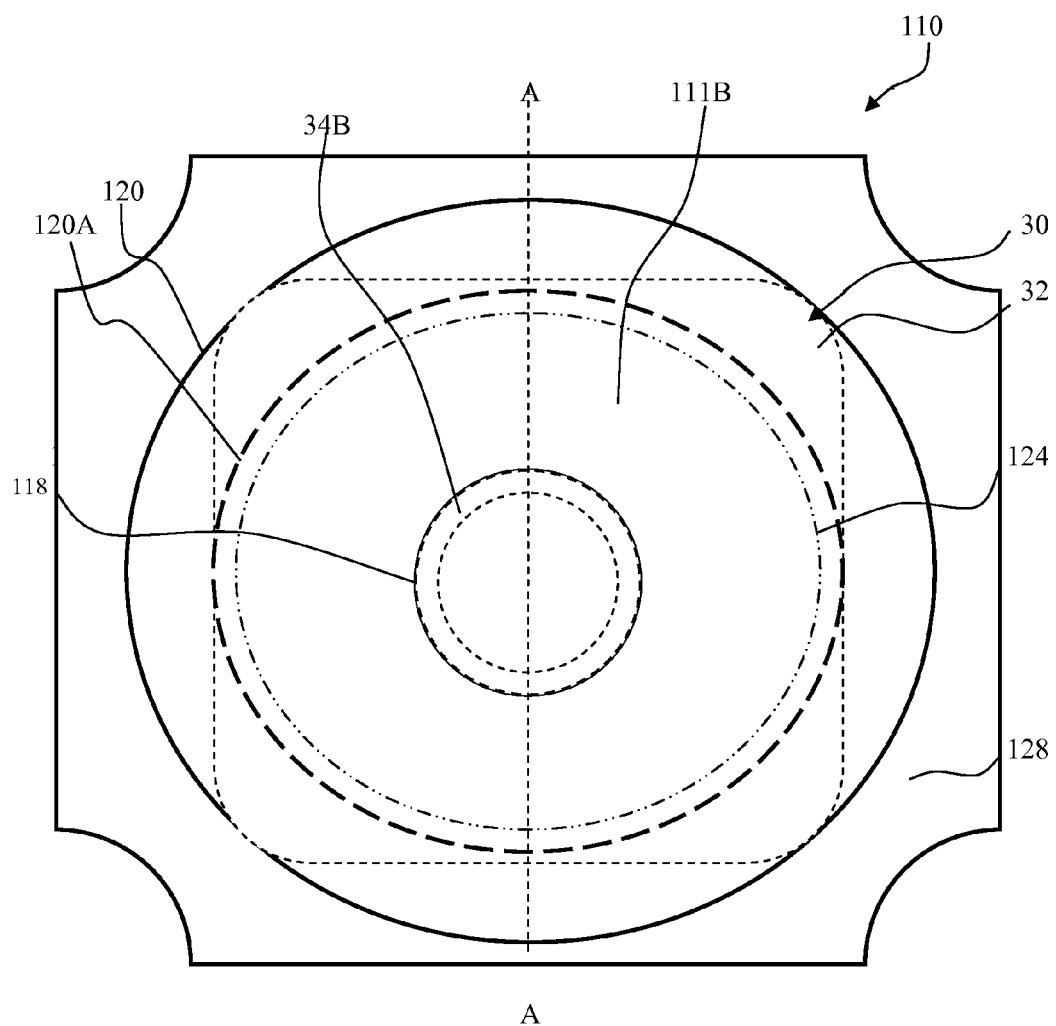
FIG. 6 is a rear view of an absorbent article of FIG. 5 showing the outer core's placement on an ostomy appliance faceplate.

FIG. 6 is a backside, or garment facing surface 111B allowing one to clearly see the position of the outer core 120 of an absorbent article 110 on a faceplate 30 of a pouching system. The conjoined absorbent article's central aperture 118 encompasses the faceplate flange 34B and the drawing includes a garment facing border 128A. It can readily be seen that a thickness in the outer core 120 is needed for the purpose of providing protection where leaks are prone to emerge, at a location anywhere along the outer taped portion 32 of a faceplate 30, said faceplate outline shown in phantom. The guard system 10/50 has a point of contact 124 on the absorbent article 110 and said contact point 124 lies adjacent the core aperture 120A as can also be seen in FIG. 6A. Pressure applied by a guard system 10/50 through the absorbent article 110 at the point of contact 124 to the faceplate 30, is more or less than about ¼ in (0.06 cm) inside the outer taped portion 32, said measurement not including the corners of this exemplary faceplate.

The fluid impermeable backsheet 114 may be made of a hydrophobic, breathable layer such as a breathable polymer or polyethylene film (embossed or not) and may include a non-woven web backing layer 121 that allows exchange of vapor or may be comprised of thermal bonding fibers used in the production of cloth-like backsheets to prevent soiling a user's clothing or linens.

The conjoined absorbent article 110 may include in the central portion 112A of topsheet 112 a relatively hydrophobic, synthetic elastomer, free of natural rubber allergens, including the central portion of the body facing surface 111A, where continuity or unity of parts surrounding central aperture 118 may be formed with sufficient elasticity to apply the article for use upon a pouching system. The backsheet 114 may, alternately, comprise a stiffening element consisting of a plastic sheet, fibrillated film used as a facing for a hydrophobic non-woven material, or a paper material with a hydrophobic surface, etc., to provide at least one ventilation area which allows the passage of vapor to provide cooling and drying effects, or to provide a stiffness in the area under a guard system 10/50 conveying durability and ease of handling while applying the article to a pouching system.

The absorbent article's central aperture 118 may otherwise be provided in varied sizes to accommodate various flange sizes of appliances, and preferably in skin tone colors so as not to be noticed under clothing. Any or all embodiments may have the centrally located aperture 118 alternately off centered with aperture 118 more toward the top of the article in order to avoid a waistband.

In the case an absorbent article 110 has an outer border 128, adhesive may be applied to the outer border 128 on the body-facing surface 111A of topsheet 112, rather than the backsheet 114, as may usually be the case on pantiliners and the like, that are normally attached to one's undergarments instead of the skin. The adhesive may be applied by attaching a one-sided tape to the garment facing border 128B of the backsheet 114 in a continuous or discontinuous configuration, and the remaining portion of the tape extending past the distal edge of outer border 128 to attach to the skin of the wearer, including a release liner (not shown) of matching configuration or conversely, may be directly applied to the outer border 128 on the body facing border 128A having a release liner positioned adjacent the adhesive in a continuous or discontinuous configuration.

Figure 6A:
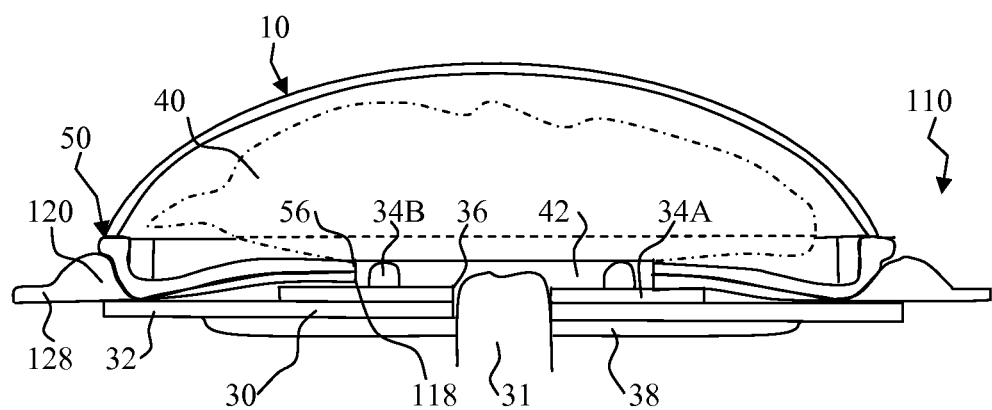
FIG. 6A is a cross sectional view of the absorbent article of FIG. 5 showing the guard system's placement on an absorbent article and it's relative position on a faceplate.

The adhesive on the outer border 128 attaching the article directly to a user's skin may be with soft skin adhesives such as are made by Dow Corning®, product numbers 7-9700 A & B, or MG7-9800 A&B used in wound dressings, where gentle adhesion to the skin is critical, with low peel release force that does not cause damage or pain to fragile skin or may have adhesion properties of over the counter bandages for those who have progressed to more advanced healing. Such adhesive may be provided on one or more flaps or on the entire distal circumference of the absorbent article 110, together with removable release liners. The adhesive release liners may be formed of any material known in the art for such purposes and may be provided in one continuous piece, but preferably in sections such as a top and bottom portion to enable a gradual application process that prevents unintended attachment to other surfaces or areas of skin. Adhesive attachment to the skin may present a more discreet profile under clothing, and also provide added security against leakage of waste. Alternately, the conjoined absorbent article may not be provided with adhesive on the outer border 128 and may be anchored by the guard system 10/50, by position of the core aperture 120A lying closely adjacent the guard system 10/50 as illustrated in FIG. 6A. The absorbent article may be individually wrapped, sealed or packaged with any suitable thermoplastic sheeting or non-woven material and carried out by any current methods known in the art.

The circular embodiment of an absorbent article as illustrated, may be appropriate for faceplate shapes that are not circular, or a square shaped absorbent article may be appropriate for a circular shaped faceplate, etc. and the illustrated embodiment is not meant in any way to limit the scope of the invention, nor is it limited to the particular types or configurations of absorbent articles shown in the drawings. Absorbent articles may be provided in various colors, sizes of small, medium or large, daytime or nighttime wear, and these variations may also be applied in alternative embodiments when used without a guard system.

Common and generally square faceplate sizes measured from their peripheral edges may range in diameter approximately more or less than about 1⅞ inch (47 mm) square (infant size), up to more or less than about 4.0 inches (100 mm) square, more or less than about 5.0 inches (127 mm) square, and up to more or less than about 6.0 (152 mm) square, or possibly larger in less common or specially ordered sizes. Circular faceplate diameters or triangular configurations in similar size ranges, as mentioned above, are also available in common sizes.

The absorbent article's central aperture 118 may be provided in various sizes. Common flange diameters of appliance faceplates generally range more or less than about 1⅞ inches (47 mm), more or less than about 1¾ inches (44 mm), more or less than about 2¼ inches (57 mm), more or less than about 2¾(70 mm), and more or less than 4.0 inches (100 mm).

The absorbent article 110 may have an overall diameter of less than or equal to about 10 inches (254 mm), preferably less than or equal to about 8½ (220 mm), more preferably less than or equal to about 6½ inches (165 mm), and of more than or equal to about 5½ inches (140 mm), and of more than or equal to about 3½ inches (90 mm). The absorbent article (without flaps or circular appendages, if any), may be preferably more than or equal to about 4.0 inches (100 mm), more preferably, more than or equal to 5½ inches (140 mm).

The absorbent article may be formed of any suitable material known in the art to provide a single use, latex free, protective pad that may be rustle-free, absorbent, strong, yet light-weight with optimal fluid (urine) absorbency and an ability to absorb viscous fluid such as watery feces or urine. The absorbent article may include layers of fibrous webs or batts constructed of defiberized, loose, hydrophilic, cellulosic fibers including wood pulp, or layers of tissue (such as wadding) and fibrated comminution pulp (airfelt) or other fiber-variant polymers.

Other possible components may include fluff pulp, super-absorbent polymers (SAP's) that lock away wetness into an odor free gel, hydrophilic surfactants, granules, flakes, odor neutralizers and bacterial growth neutralizers, antimicrobial agents or other additives to impart flame retardancy, softness or color, impervious plastic films having vapor permeability, impervious backing films, liquid pervious acquisition sheets, pad release liners, carded non-wovens, pressure sensitive adhesives and elastics or any components that may be suitable to be worn on the abdomen of a user.

The article may be formed by any suitable processes that may provide thermobonded webs (carded or wetlaid webs or spunbonds and can be thermal bonded with synthetic bonding fibers (generally with bi-components of polyethylene and polypropylene or polyolefin copolymers), or through air bonding; drylaid or airlaid, hydroentangled, spunlaced, or spunmelt, or of either process: spunlaid or meltblown; or including other processes, such as modifying or varying any combination of controllable manufacturing parameters such as spinneret properties or altering spin finish, etc., or embossing, calendering, or any other processes that may be known in the art, including any and all other elements or processes added that do not affect the end result provided that the absorbent article 110 has the overall characteristics described herein.

Figure 7:
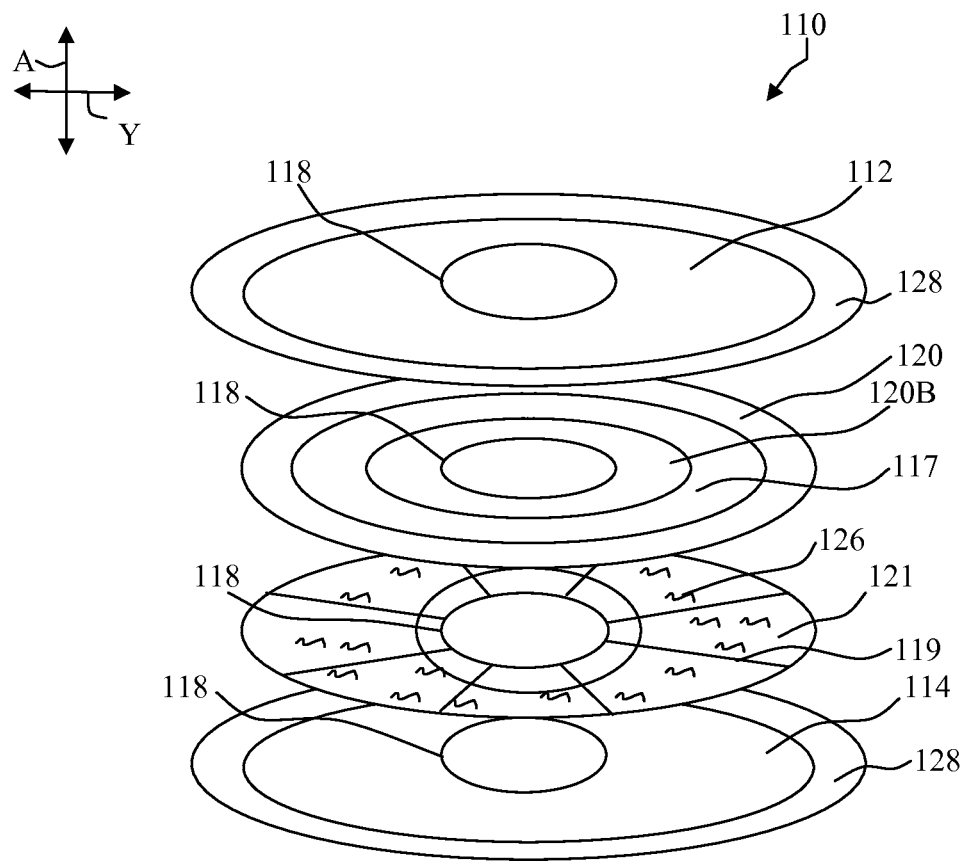
FIG. 7 is a perspective view of a second embodiment of an absorbent article.

FIG. 7 illustrates a second embodiment of the absorbent article when worn without a guard system 10/50, consisting of a fluid permeable top sheet 112, a fluid impermeable backsheet 114, an outer border 128, and layers of a thick outer core 120, a thick inner core 120B and absorbent core 121 interposed between; central aperture 118 maintains said articles position on a faceplate 30. The thick outer core 120, has a thickness equivalent to a thick inner core 120B which lies adjacent to central aperture 118, and inner core 120B is positioned on the same plane as outer core 120, and outer core 120 and inner core 120B have a thickness greater than absorbent core 121, in this embodiment; absorbent core 121 is positioned under outer core 120 and inner core 120B, and absorbent core 121 is positioned on top of backsheet 114. Alternately, cores 120, 120B and 121 may be one layer with varied degrees of thickness. Leaking effluent from under a faceplate 30 is blocked from escaping the outer boundary of the absorbent article 110 by means of the outer core 120 positioned outside the peripheral edges of a faceplate 30, including an outer border 128 that may or may not be adhesively attached to the skin of the wearer. Effluent not immediately absorbed by the outer core 120 may be diverted inwardly toward the thick inner core 120B by means of transverse wicking in continuous or discontinuous lines or compression channels 119 formed by hot calender embossing or ultrasonic means, heat compression, etc. and escaping effluent is temporarily contained in a pocket 117 between the thick cores 120 and 120B on an undulated surface 126 of the absorbent core 121, constructed of components such as fluff pulp, SAP's etc., absorbent components may be included in all absorbent core layers as needed, to aid containment of effluent, at least temporarily, allowing one time to effect a change of incontinent apparatuses before leakage soils clothing or linens.

Figure 8:
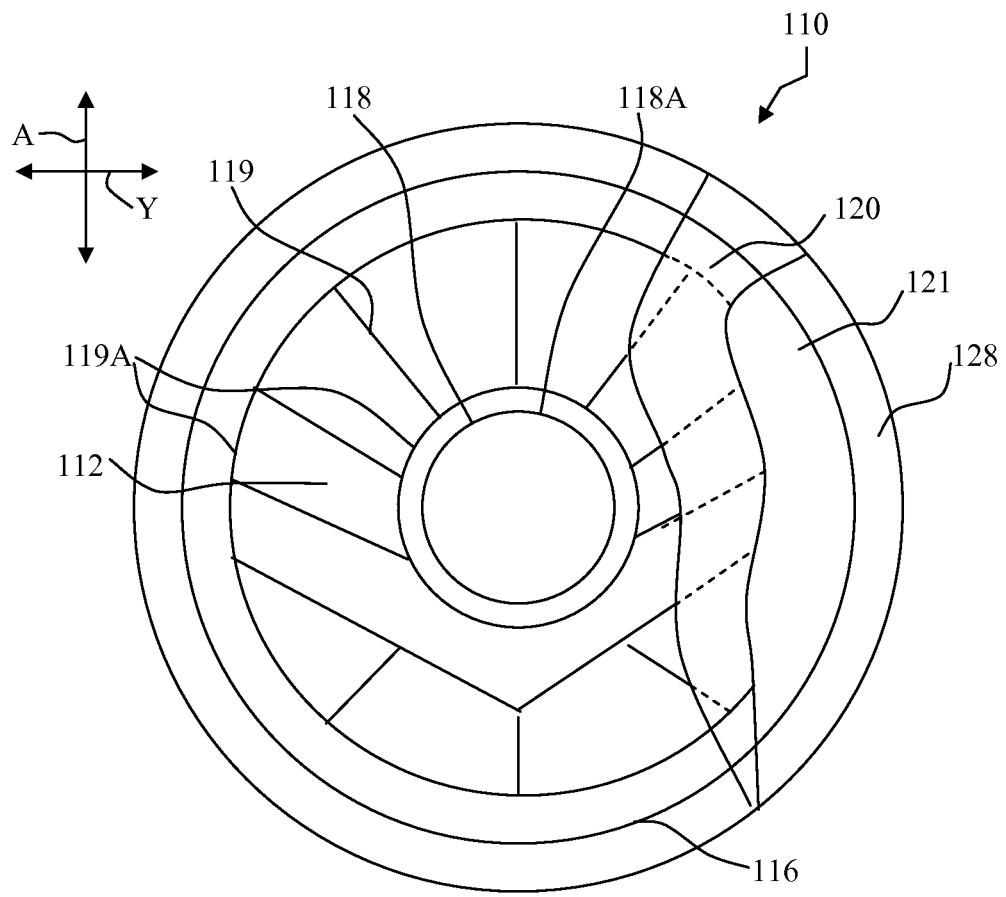
FIG. 8 is a third embodiment of an absorbent article.

In a third embodiment shown in FIG. 8, worn under form-fitted clothing and without a guard system 10/50, consisting of a fluid permeable top sheet 112, a fluid impermeable backsheet 114 (not shown), an outer border 128, and a thick outer core 120, which has a consistent thickness throughout, including a method of absorbing, drawing or wicking a sudden assault of escaping effluent inwardly toward the central aperture 118, over top of a faceplate by means of a plurality of compression channels 119 formed by hot calender embossing, ultrasonic means, or heat compression, etc. through all layers of the absorbent article 110, including one or more outer and inner circular compressions 119A directly above the outer periphery of a faceplate 30 and close to central aperture 118 to prevent effluent from escaping outside of the absorbent article 110. It has been contemplated that compression lines create a pie-shaped configuration to draw effluent inwardly as shown in FIG. 7A. Furthermore, it may be possible to designate top and bottom portions of an absorbent article by creating a significantly different shape in the outer border 128 on one or more sides for the purpose of providing compression lines 119 that allow output to adhere to laws of gravity wherein said compression lines are angled in a downward fashion along the sides. It has also been contemplated that central aperture 118 has an elastic means 118A to help retain the captured output.

One further contemplation is the addition of a type of skin prep using some, none or all ingredients of Isopropyl Alcohol, Butyl Ester of PVM/MA Copolymer, Acetyl Tributyl Citrate which are the ingredients in Skin Prep° made under the trademark Smith & Nephew of St. Petersburg, Fla., and supplied in a form that might be sprayed on the body-facing surface 111A of topsheet 112, during manufacture to provide protection for exposed skin beneath an absorbent article 110 in an area immediately adjacent a faceplate periphery. In its intended use, Skin Prep° forms a film coating on the skin and after it is applied, the user waits until it is dry before applying a skin friendly hydrocolloid containing, adhesive faceplate of an ostomy appliance creating a barrier that protects the skin under a faceplate from irritating digestive juices. Skin Prep° also prevents skin stripping upon removal of a faceplate. It has been found that once Skin Prep° is applied to the skin and has dried, the absorbent article does not stick to the skin as in the case when used with a faceplate with adhesive. Therefore, it has been contemplated possible to apply a type of skin prep to a non-woven material to provide skin protection for a user.

While the invention has been particularly shown and described with respect to preferred embodiments, it will be readily understood that minor changes in the details of the invention may be made without departing from the spirit of the invention.

Having described the invention, I claim:

1. An absorbent article for use with an ostomy appliance, comprising:
    a core structure having a front surface and a body facing surface and two layers of absorbent material, said core structure having:
        a first layer of absorbent material having a first thickness and a first aperture with a first diameter, said first layer of absorbent material having contour features including compression channels extending into said absorbent material and extending radially outwardly from said first aperture toward exterior edge of the absorbent article to draw fluid toward a central area of said absorbent article,
        a second layer of absorbent material with a second thickness and a second aperture having a second diameter, said second thickness being substantially greater than said first thickness and said second diameter of said second aperture being substantially greater than said first diameter,
        said first and second layers of absorbent materials having greater fluid permeability near said apertures and less fluid permeability away from said apertures, said greater thickness of said second layer of absorbent material at said second diameter creating a thicker absorbent barrier substantially near the perimeter defined by said second diameter to prevent leakage;
    a fluid permeable top sheet, having an outer border and a third thickness and a third aperture with said first diameter, placed on said body facing surface of said core structure;
    a fluid impermeable back sheet, having an outer border and a fourth thickness and a fourth aperture with said first diameter, placed on said front surface of said core structure, said outer border of said fluid permeable top sheet and said outer border of said fluid impermeable back sheet are secured together to enclose said two layers of absorbent material in said core structure between said fluid permeable top sheet and said fluid impermeable back sheet; and wherein said fluid permeable top sheet and said fluid impermeable back sheet both have a corresponding aperture located and adapted to surround an ostomy appliance flange.

2. The absorbent article of claim 1, wherein said core structure has a varied degree of thickness said core structure having less thickness near said ostomy appliance aperture and greater thickness beyond the periphery of said ostomy appliance faceplate such that more of said absorbent material is disposed on said periphery of said core structure than near said aperture.

3. The absorbent article of claim 1, wherein said third thickness and said fourth thickness are substantially the same as said first thickness, and said second thickness of said absorbent materials has a thickness greater than said first, third and fourth thicknesses.

4. The absorbent article of claim 1, wherein said core structure has a greater thickness in an area that extends beyond said periphery of said ostomy appliance faceplate said thickness extending beyond said ostomy appliance faceplate being situated for absorbing and blocking any liquid seepage that may emerge from said faceplate.

5. The absorbent article of claim 1, wherein the diameter of said absorbent article ranges from 3.5 inches to 10 inches.

6. A method of making an absorbent article for use with an ostomy appliance, comprising the steps of:

providing a core structure having a front surface and a body facing surface, said core structure having two layers of absorbent material that include a first layer of absorbent material having a first thickness and a first aperture with a first diameter, said first layer of absorbent material having contour features with compression channels extending into said absorbent material and extending radially outwardly from aperture toward exterior edge of the absorbent article to draw fluid toward a central area of said absorbent article, and a second layer of absorbent material with a second thickness and a second aperture having a second diameter, said second thickness being substantially greater than said first thickness, and said second diameter being substantially greater than said first diameter, said greater thickness of said second layer of absorbent material at said second diameter creating a thicker absorbent barrier substantially near the perimeter defined by said second diameter to prevent leakage;

placing a fluid permeable top sheet on said body facing surface of said core structure, said fluid permeable top sheet having an outer border and a third thickness and a third aperture with said first diameter, said third aperture located and adapted to surround an ostomy appliance flange;

placing a fluid impermeable back sheet on said front surface of said core structure, said fluid impermeable back sheet having an outer border and a fourth thickness and a fourth aperture with said first diameter, said fourth aperture located and adapted to surround an ostomy appliance flange; and securing together said outer border of said fluid permeable top sheet and said outer border of said fluid impermeable back sheet to enclose said core structure between said fluid permeable top sheet and said fluid impermeable back sheet.

7. The method of claim 6, wherein core structure has a varied degree of thickness said core structure having less thickness near said ostomy appliance aperture and greater thickness beyond the periphery of said ostomy appliance faceplate such that more of said absorbent material is disposed on said periphery of said core structure than near said aperture.

8. The method of claim 6, wherein said third thickness and said fourth thickness are substantially the same as said first thickness, and said second thickness of said absorbent materials has a thickness greater than said first, third and fourth thicknesses.

9. The method of claim 6, wherein said core structure has a greater thickness in an area that extends beyond said periphery of said ostomy faceplate said thickness extending beyond said ostomy appliance faceplate being situated for absorbing and blocking any liquid seepage that may emerge from said faceplate.

10. The method of claim 6, wherein said absorbent materials have greater fluid permeability near said aperture and less fluid permeability away from said aperture.

11. The method of claim 6, wherein the maximum diameter of said absorbent article ranges from 3.5 inches to 10 inches.

12. An absorbent article for use with an ostomy appliance, comprising:

a core structure made of a first and second layer of absorbent material, said core structure having a front surface and a body facing surface, said first layer of absorbent material having a first thickness and a centrally located first aperture with a first diameter, said first layer of absorbent material having contour features including compression channels extending into said fluid absorbent material and extending radially outwardly from said first aperture toward exterior edge of the absorbent article to draw fluid toward a central area of said absorbent article, said second layer of absorbent material having a second thickness and a second aperture with a second diameter, said second thickness being substantially greater than said first thickness and said second diameter being substantially greater than said first diameter, said greater thickness of said second layer of absorbent material at said second diameter creating a thick absorbent barrier substantially near the perimeter defined by said second diameter to prevent leakage;

a fluid permeable top sheet, having an outer border, and a third thickness and a third aperture with said first diameter, placed on said body facing surface of said core structure;

a fluid impermeable back sheet, having an outer border, and a fourth thickness and a fourth aperture with said first diameter placed on said front surface of said core structure, said outer border of said fluid permeable top sheet and said outer border of said fluid impermeable back sheet are secured together to enclose said two layers of absorbent material in said core structure between said fluid permeable top sheet and said fluid impermeable back sheet; and wherein said fluid permeable top sheet and said fluid impermeable back sheet both have a corresponding centrally located aperture adapted to surround an ostomy appliance flange.

13. The absorbent article of claim 12, wherein said core structure comprises various thicknesses said core structure having less thickness near said ostomy appliance aperture and greater thickness beyond said periphery of said ostomy appliance faceplate such that more of said fluid absorbent material is disposed on the periphery of said core structure than near said aperture.

14. The absorbent article of claim 12, wherein said core structure comprises two or more fluid absorbent materials secured to one another.

15. The absorbent article of claim 12, wherein said third thickness and said fourth thickness are substantially the same as said first thickness, and said second thickness of said absorbent materials has a thickness greater than said first, third and fourth thicknesses.

16. The absorbent article of claim 12, wherein said core structure has a greater thickness in an area that extends beyond said periphery of said ostomy appliance faceplate said thickness extending beyond said ostomy appliance faceplate being situated for absorbing and blocking any liquid seepage that may emerge from said faceplate.

17. The absorbent article of claim 12, wherein said absorbent materials in said core structure have greater fluid permeability near said aperture and less fluid permeability away from said aperture.

18. The absorbent article of claim 12, wherein the maximum diameter of said absorbent article ranges from 3.5 inches to 10 inches.

19. The absorbent article of claim 12, wherein said absorbent article is adapted for use with an ostomy guard device as an absorbent article between said ostomy appliance and said ostomy guard device.

\* \* \* \* \*

UNITED STATES PATENT AND TRADEMARK OFFICE
CERTIFICATE OF CORRECTION

| | | |
|---|---|---|
| PATENT NO. | : 9,084,696 B2 | Page 1 of 1 |
| APPLICATION NO. | : 13/841269 | |
| DATED | : July 21, 2015 | |
| INVENTOR(S) | : Donna E. Luce | |

It is certified that error appears in the above-identified patent and that said Letters Patent is hereby corrected as shown below:

In the specification

Figure 2A:
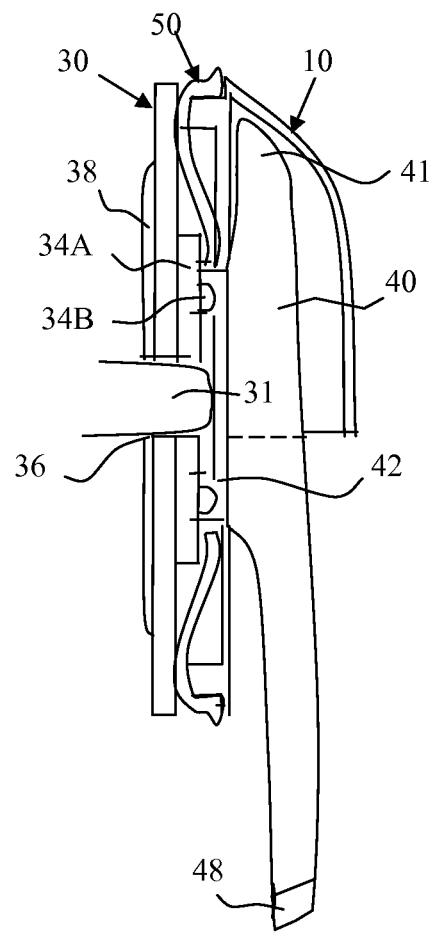
FIG. 2A is a cross sectional view of a guard system of FIG. 2 on an ostomy appliance.

Col. 3, Lines 32-33 - Remove "(44B not shown)"
Col. 3, Line 33 - After "tab" insert --46--
Col. 4, Line 18 - After the word "stoma 31", add "as can be seen in FIG. 2A."

Signed and Sealed this
Fifteenth Day of December, 2015

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 9,084,696 B2 | Page 1 of 2 |
| APPLICATION NO. | : 13/841269 | |
| DATED | : July 21, 2015 | |
| INVENTOR(S) | : Luce | |

It is certified that error appears in the above-identified patent and that said Letters Patent is hereby corrected as shown below:

Delete the title page and substitute therefore with the attached title page consisting of the corrected illustrative figure.

Signed and Sealed this
Twenty-third Day of February, 2016

Michelle K. Lee
*Director of the United States Patent and Trademark Office*

CERTIFICATE OF CORRECTION (continued)

(12) United States Patent
Luce

(10) Patent No.: US 9,084,696 B2
(45) Date of Patent: Jul. 21, 2015

(54) ABSORBENT ARTICLE FOR AN OSTOMY GUARD

(71) Applicant: Donna E. Luce, Duncanville, TX (US)

(72) Inventor: Donna E. Luce, Duncanville, TX (US)

(*) Notice: Subject to any disclaimer, the term of this patent is extended or adjusted under 35 U.S.C. 154(b) by 211 days.

(21) Appl. No.: 13/841,269

(22) Filed: Mar. 15, 2013

(65) Prior Publication Data

US 2014/0276519 A1    Sep. 18, 2014

(51) Int. Cl.
- *A61F 13/15* (2006.01)
- *A61F 5/44* (2006.01)
- *A61F 13/02* (2006.01)
- *A61F 13/00* (2006.01)

(52) U.S. Cl.
CPC .... *A61F 13/02* (2013.01); *A61F 5/44* (2013.01); *A61F 2013/00412* (2013.01)

(58) Field of Classification Search
CPC .... A61F 5/44; A61F 5/4401; A61F 2005/4402
USPC ................... 604/361, 33, 333, 334
See application file for complete search history.

(56) References Cited

U.S. PATENT DOCUMENTS

| | | |
|---|---|---|
| 1,922,763 A | 8/1933 | Gricks |
| 2,129,054 A | 9/1938 | Geisler |
| 2,496,175 A | 1/1950 | Perry |
| 2,549,649 A | 4/1951 | Van Hove |
| 2,656,838 A | 10/1953 | McConnell |
| 2,675,002 A | 4/1954 | Cesare |
| 2,837,094 A | 6/1958 | Cowles |
| 3,074,404 A | 1/1963 | Robinson |
| 3,398,744 A | 8/1968 | Hooper |
| 4,596,566 A | 6/1986 | Kay |
| 4,636,206 A | 1/1987 | Federati |
| 4,723,952 A | 2/1988 | Esposito |
| 4,738,257 A | 4/1988 | Meyer |
| 4,867,749 A | 9/1989 | Steer |
| 5,125,917 A | 6/1992 | Whealin |
| 5,178,614 A | 1/1993 | McDowell |
| 5,203,806 A * | 4/1993 | Broida ............... 604/338 |
| 5,338,315 A | 8/1994 | Baker |
| 5,653,701 A | 8/1997 | Millman |
| 5,811,116 A | 9/1998 | Gilman |
| 6,129,715 A | 10/2000 | Cunningham |
| 8,316,985 B2 | 11/2012 | Bain et al. |
| 2007/0135783 A1 | 6/2007 | Scott |
| 2010/0191202 A1 | 7/2010 | Hogard et al. |
| 2010/0241093 A1 | 9/2010 | Hooper |

FOREIGN PATENT DOCUMENTS

WO    9716141    5/1997

* cited by examiner

*Primary Examiner* — Jacqueline Stephens
(74) *Attorney, Agent, or Firm* — Hemingway & Hansen, LLP; D. Scott Hemingway

(57) ABSTRACT

A disposable absorbent article for use with ostomy appliances and complementary to a guard system such as has been illustrated, that provides an additional level of security and comfort to an ostomate already utilizing a two-piece or one-piece ostomy appliance of the type which is secured to the body with a faceplate comprising an adhesive securement means such as a hydrocolloid adhesive member or a combination of hydrocolloid adhesive member and an integral or non-integral adhesive non-woven fabric or adhesive tape.

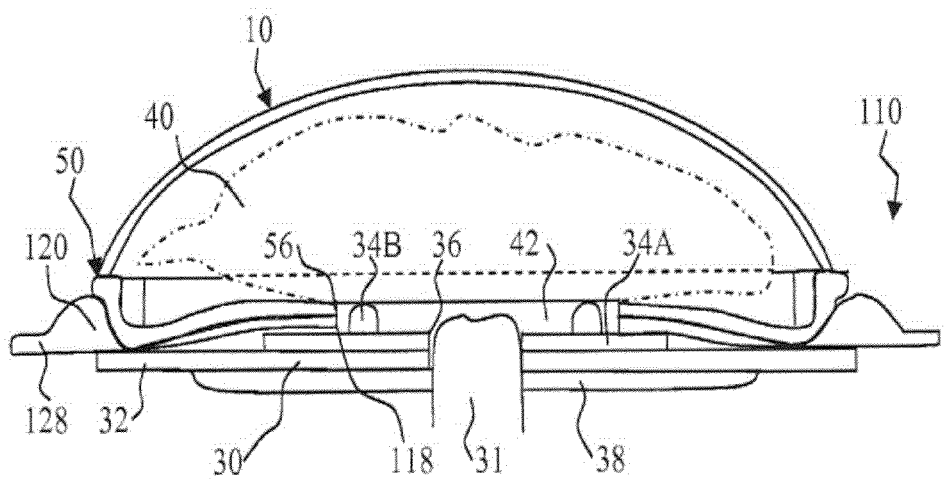

19 Claims, 10 Drawing Sheets